United States Patent
Puma et al.

(10) Patent No.: US 7,288,057 B1
(45) Date of Patent: Oct. 30, 2007

(54) METHOD FOR CONDITIONING TO PREVENT MOTION SICKNESS

(76) Inventors: Samuel C. Puma, 32600 Flight Way, Winchester, CA (US) 92596; Susan W. Puma, 32600 Flight Way, Winchester, CA (US) 92596

( * ) Notice: Subject to any disclaimer, the term of this patent is extended or adjusted under 35 U.S.C. 154(b) by 336 days.

(21) Appl. No.: 10/885,853

(22) Filed: Jul. 7, 2004

Related U.S. Application Data

(60) Provisional application No. 60/485,601, filed on Jul. 7, 2003.

(51) Int. Cl.
*A63B 71/00* (2006.01)

(52) U.S. Cl. .......................... 482/148; 600/25; 600/26; 128/747; 128/897; 348/148

(58) Field of Classification Search ................ 128/747, 128/897, 845, 898, 400–401, 151; 600/25–28, 600/595, 484, 546; 381/313, 98, 309, 103; 482/148; 702/150; 137/38; 340/945, 967; 84/720; 273/449; 473/221; 348/148
See application file for complete search history.

(56) References Cited

U.S. PATENT DOCUMENTS

| | | | | |
|---|---|---|---|---|
| 6,004,243 A * | 12/1999 | Ewert | ............................ | 482/8 |
| 6,042,533 A * | 3/2000 | Kania | ........................... | 600/27 |
| 6,228,021 B1 * | 5/2001 | Kania | ........................... | 600/27 |
| 6,443,913 B1 * | 9/2002 | Kania | ........................... | 600/595 |
| 6,468,086 B1 * | 10/2002 | Brady-Koontz | ............. | 434/257 |
| 6,568,396 B1 * | 5/2003 | Anthony | ...................... | 128/897 |
| 6,609,523 B1 * | 8/2003 | Anthony | ...................... | 128/897 |
| 6,692,428 B1 * | 2/2004 | Kania | ........................... | 600/27 |
| 6,758,218 B2 * | 7/2004 | Anthony | ...................... | 128/897 |
| 7,128,705 B2 * | 10/2006 | Brendley et al. | ............. | 600/27 |
| 2001/0000459 A1 * | 4/2001 | Kania | ........................... | 381/98 |
| 2003/0116166 A1 * | 6/2003 | Anthony | ...................... | 128/897 |
| 2005/0019735 A1 * | 1/2005 | Demas | ........................ | 434/247 |

* cited by examiner

*Primary Examiner*—Lori Amerson
(74) *Attorney, Agent, or Firm*—Kenneth L. Green; Edgar W. Averill, Jr.

(57) ABSTRACT

Easily performed exercises quickly raise the tolerance to motion sickness and do not require supervision. The exercises are comprised of a warm-up phase and a conditioning phase. The warm-up phase includes a series of rotation and tilting exercises which both warm-up the muscles and joints, and provide some degree of conditioning. The conditioning exercises are directed to specific motion sickness causing movements and provide direct and powerful conditioning to overcome motion sickness. The exercises requires about fifteen minutes each day, and provide substantial relief from motion sickness in as little as two weeks. A demonstrator may be recorded on recording media performing the exercises, and the exercises are preferably self taught by a user viewing the recorded demonstration.

22 Claims, 7 Drawing Sheets

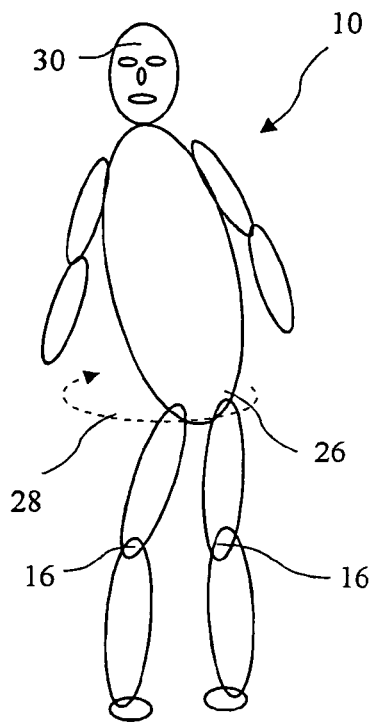
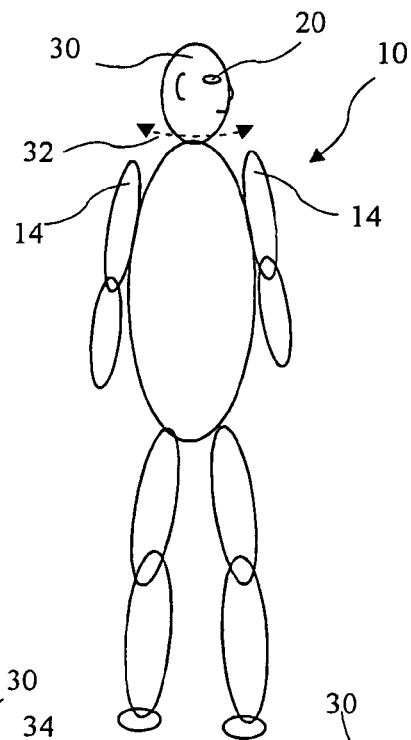
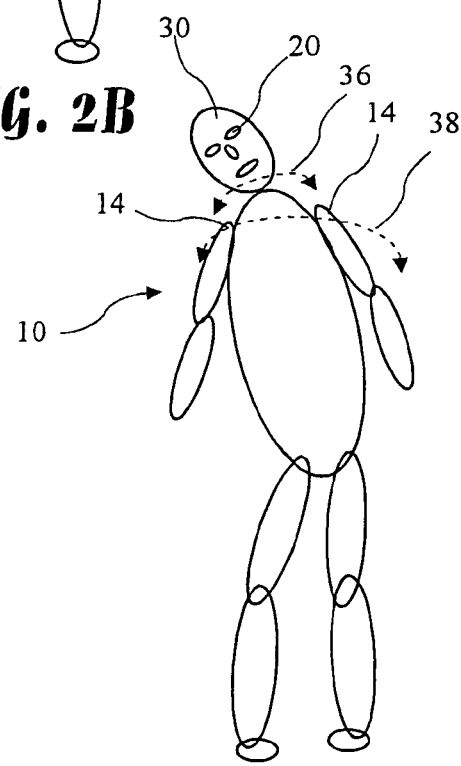
FIG. 2A  FIG. 2B  FIG. 2C  FIG. 2D

METHOD FOR CONDITIONING TO PREVENT MOTION SICKNESS

The present application claims the benefit of U.S. Provisional Application Ser. No. 60/485,601, filed Jul. 7, 2003, which application is incorporated herein by reference.

BACKGROUND OF THE INVENTION

The present invention relates to the prevention of motion sickness and more particularly to a set of exercises which condition a human to prevent the symptoms of motion sickness.

Motion sickness is a normal response by the body which occurs when the brain receives too many or conflicting messages which relate to motion. The eyes are important sensors which visually record our position in the world relative to other objects. These objects may actually exist or simply be images on a screen. In muscles and joints, are other sensors (e.g., nerves) which provide information to the brain about the position and movement of our body. Perhaps the most important sensors are the fluid filled structures called the semi-circular canals which are located in each ear. Inside these canals, there are tiny hair cells which are stimulated when the head moves. The brain continually receives messages from all of these sensors.

Normally, the brain has no difficulty in appropriately processing all of these messages, and we pursue our various activities with no ill effects. However, if the brain is overwhelmed with too much and conflicting sensory information, the body responds with the symptoms of motion sickness. These symptoms include nausea, lightheadedness and headache. Motion sickness can also occur when a continuing repetitive pattern of motion is different from that normally experienced.

Motion sickness is commonly experienced when riding in a moving vehicle such as a car, boat, airplane, or amusement park ride, and many other activities. Motion sickness symptoms can also occur when a visual perception indicates that motion is taking place but the body is not in fact moving. A good example of this is when a person is viewing a very large screen motion picture of a rider's view of a roller coaster ride, while seated in a theater such as an IMAX. There are numerous drugs and devices which have been used to reduce or eliminate motion sickness, but to date, all of these known solutions have disadvantages. For example, a commonly used patch may cause side effects such as nightmares. Some drugs cause extreme drowsiness, and most physical devices, such as pressure bracelets, are not particularly effective.

Other methods, such as visual-vestibular habituation exercises and balance training, involve exposure to the motion sickness causing conditions to develop a tolerance to such conditions. Although known methods have provided some relief, they generally require active supervision, may take months to achieve significant results, and may not provide a complete solution.

BRIEF SUMMARY OF THE INVENTION

The present invention addresses the above and other needs by providing easily performed daily exercises which raise the tolerance to motion sickness. The daily exercises include a warm-up phase and a conditioning phase. The warm-up phase is comprised of a series of rotation and tilting exercises which both warm up the muscles and joints, and provide some degree of conditioning. The conditioning exercises are directed to specific motion sickness causing movements and provide direct and powerful conditioning to overcome motion sickness. The exercises require about fifteen minutes each day, and provide substantial relief from motion sickness in about two weeks. A demonstrator may be recorded on recording media performing the exercises, and the exercises are preferably self taught by a user viewing the recorded demonstration.

In accordance with one aspect of the invention, a motion sickness exercise program is provided involving motion of the central body, head, upper body, hips, and arms. The exercises include warm-up exercises and conditioning exercises. The warm-up exercises are performed with back straight, shoulders relaxed, knees slightly bent, feet about shoulder width apart, and eyes kept open and looking forward. The warm-up exercises entail performing specific repetitive body movements: 1. a hip rotation exercise; 2. a horizontal head rotation exercise; 3. a vertical head tilt exercise; and 4. a lateral head tilt exercise. The hip rotation exercise is performed about ten times to the right and about ten times to the left. A first set of about ten repetitions of the horizontal head rotation exercise, about ten repetitions of a vertical head tilt exercise, and about ten repetitions of a lateral head tilt exercise is performed. Next, a second set of about ten repetitions of the horizontal head rotation exercise, about ten repetitions of the vertical head tilt exercise, and about ten repetitions of lateral head tilt exercise is performed. The warm-up exercises are completed by performing a third set of about ten repetitions of the horizontal head rotation exercise, about ten repetitions of the vertical head tilt exercise, and about ten repetitions of lateral head tilt exercise.

The conditioning exercises are composed of a spiral exercise and a figure eight exercise. The spiral exercise is accomplished by rotating the hips, the upper body, and the head together in a clockwise motion while bending forward, to the side, and back, and after at least three rotations, spiraling to a vertical stop. The spiral exercise is then repeated in exactly the same way, but in a counterclockwise direction. The spiral exercise should be practiced gradually over a period of days until it can be done three times in each direction without feeling symptoms of motion sickness. The figure eight exercise is accomplished by moving the head, neck, and upper body in a figure eight pattern. First perform the motion with an upward sweep of the head on the ends of the figure eight. Trace six figures of eight then stop abruptly at the center point. Do another six figures of eight performing a downward sweep of the head on the ends of the figure eight, again stopping abruptly at the center point. In this manner, do the figure eight exercises two more times for a total of three repetitions in each direction. For the purposes of these exercises, it is understood that the figure eight is laying on it's side, i.e., a lazy eight.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 2A shows a hip rotation warm-up exercise according to the present invention.

FIG. 2B shows a horizontal head rotation warm-up exercise according to the present invention.

FIG. 2C shows a vertical tilt warm-up exercise according to the present invention.

FIG. 2D shows a lateral tilt warm-up exercise according to the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

The foundation of the method of the present invention is conditioning. Conditioning is accomplished by exercises which are simple, safe and effective, and take only about 15 minutes each day for as little as two weeks. The exercises may be carried out without supervision by simply following instructions provided on a recorded media, and the entire program may be self monitoring by the user. Some persons may notice significant improvement in their symptoms after only one week, but typically at least two weeks are required to receive the full benefits of the conditioning exercises. The exercises should be carried out without the use of anti-motion sickness medications or devices or drugs which produce drowsiness, including alcoholic beverages. These may prevent the conditioning exercises from being affective. It is also important that the user check with his or her family physician before altering medications and make sure there are no medical conditions that would prevent the user from doing the exercises safely.

Figure 1A:
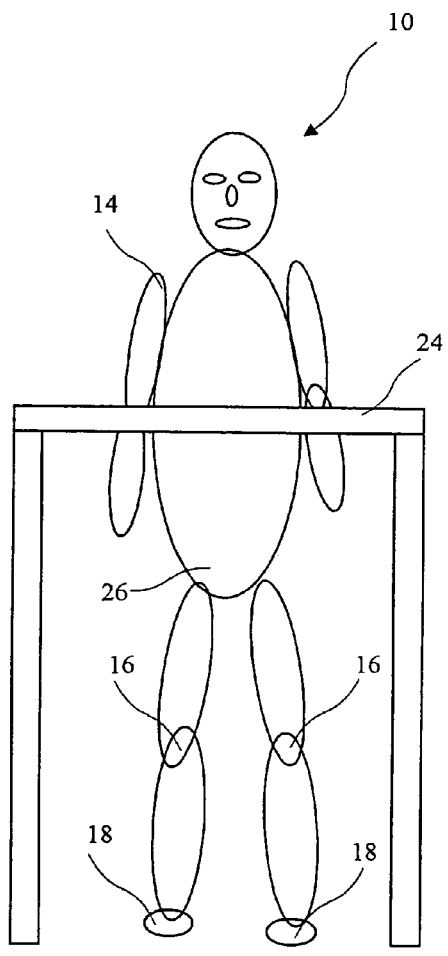
FIG. 1A shows a front view of a user prepared to perform exercises according to the present invention.
Figure 1B:
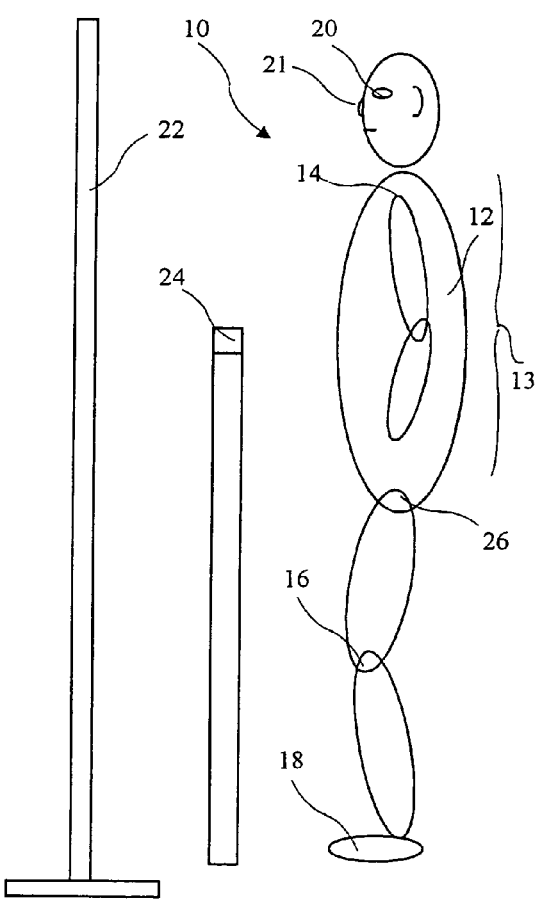
FIG. 1B shows a side view of the user prepared to perform the exercises according to the present invention

The exercises, if done correctly, should make the user feel somewhat queasy and/or dizzy (e.g., a feeling of mild nausea, uneasiness, slight disorientation, etc.,) but these sensations will disappear quickly. Such a feeling is part of the conditioning process. If the queasy and/or dizzy feeling lasts for more than a few minutes or is moderate to severe, the exercises should be stopped for the day and started again the next day. It is preferred that the exercise routine be done just before going to bed A user 10 prepared to perform the conditioning of the present invention is shown in front view in FIG. 1A, and in side view in FIG. 1B. In order to do the exercises, the user 10 should preferably stand with the user's back 12 straight, shoulders 14 relaxed, knees 16 slightly bent and feet 18 about shoulder width apart. The user's eyes 20 should be kept open and looking forward, preferably in line with the nose 21. It may be preferable to do the exercises in front of a mirror 22 so that the user 10 can see if the movements are being done correctly. It is also possible to perform most of the exercises while seated, but conditioning may take a little longer.

A support 24, for example, the padded back of a chair, preferably should be positioned in front of the user 10 for support should the user 10 become queasy and/or dizzy during the exercises, at least until the user 10 is accustom to the exercises. The user 10 may become slightly disoriented when initially doing these exercises and if a support 10 is not available, an assistant may stand by to assist the user 10, if necessary.

The conditioning commences with warm-up exercises which are comprised of a hip rotation exercise, and three head and neck exercises. The head and neck exercises include a horizontal head rotation exercise, a vertical tilt exercise, and a lateral tilt exercise. The warm-up exercises both warm up the muscles and joints, and contribute to the conditioning process.

The warm-up exercises are succeeded by two conditioning exercises. The conditioning exercises comprise a spiral exercise and a figure eight exercise. The conditioning exercises are highly effective and, if done correctly, will quickly raise the user's tolerance level to certain motions. Both warm-up exercises and conditioning exercises are preferably done at the user's own pace. Preferably, the exercises should not be done more frequently or for a longer period of time than recommended. To do so may produce severe motion sickness. When done at the user's own pace, and as recommended, the exercises produce a gradual conditioning.

The first warm-up exercise is the hip rotation exercise shown in FIG. 2A. Keeping knees 16 bent, the user 10 moves his or her hips 26 in a circle 28 (i.e., performs hip rotations) in a substantially horizontal plane (i.e., the user 10 should attempt to keep the motion in the horizontal plane, but small deviations are acceptable). A preferred duration is ten rotations 28 to the right (clockwise) and then ten to the left (counter clockwise.) The hip rotation 28 resembles a "hula hoop" like motion. The hip rotation exercise is performed once at the beginning of the warm-up, and is important to properly prepare for the spiral exercise described below (see FIG. 4).

The next warm-up exercise is the horizontal head rotation (e.g., turning the head 30 to look right and then left) exercise shown in FIG. 2B. Using a count of four, the user 10 performs head rotations by rotating the head 30 along a first arc 32 to the right, pauses, back to the center, pauses, then left, pauses, and back to center. The user 10 should pause briefly at each count point and preferably count aloud to keep track of how many repetitions have been done. The shoulders 14 are preferably substantially fixed (i.e., the only shoulder motion is that caused by the head motion) during the horizontal head rotation.

The third warm-up exercise is the vertical tilt (e.g., tilting the head to look down and forward, and then to look up and forward) exercise shown in FIG. 2C. The user's back 12 should be straight, shoulders 14 relaxed, knees 16 slightly bent and eyes 20 open. Again using a count of four, the user 10 performs a head vertical tilt by tilting the head 30 along a second arc 34 down, pauses, forward, pauses, up, pauses, and back to the forward position. The user 10 should pause briefly on each count point. The shoulders 14 are preferably substantially fixed during the vertical tilt exercise.

The last warm-up exercise is the lateral tilt (e.g., tilting the head to the right side and then to the left side) exercise shown in FIG. 2D. The user's eyes 20 should again be open. The user 10 should be relaxed and try not to lift his or her shoulders 14, although some upper body movement along a fourth arc 38 is acceptable with the lateral tilt exercise, unlike with the horizontal head rotation and the vertical tilt exercises. With a count of four, the user tilts (or leans) the user's head 30 right, as if to touch the ear to the shoulder 14, pauses, then back to center. Next, the head 30 is tilted (or leaned) left, pauses, and again back to center, along a third arc 36. The lateral tilt should be done only as far as the user 10 feels comfortable.

Preferably, each day, the user begins the warm-up with one set of the hip rotation exercise, followed with three sets of the three head and neck exercises, preferably in the order described above. Each set should contain ten repetitions of each exercise. On the first day, the sets should all be done slowly. On the following days, the user should try to increase the pace of the exercises on the second and third sets until the second set can be done at a moderate pace, and the last set more vigorously. Results will be achieved even if all the exercises can only be done slowly, although it is likely to take a longer time to build up tolerance to certain motions.

Figure 3:
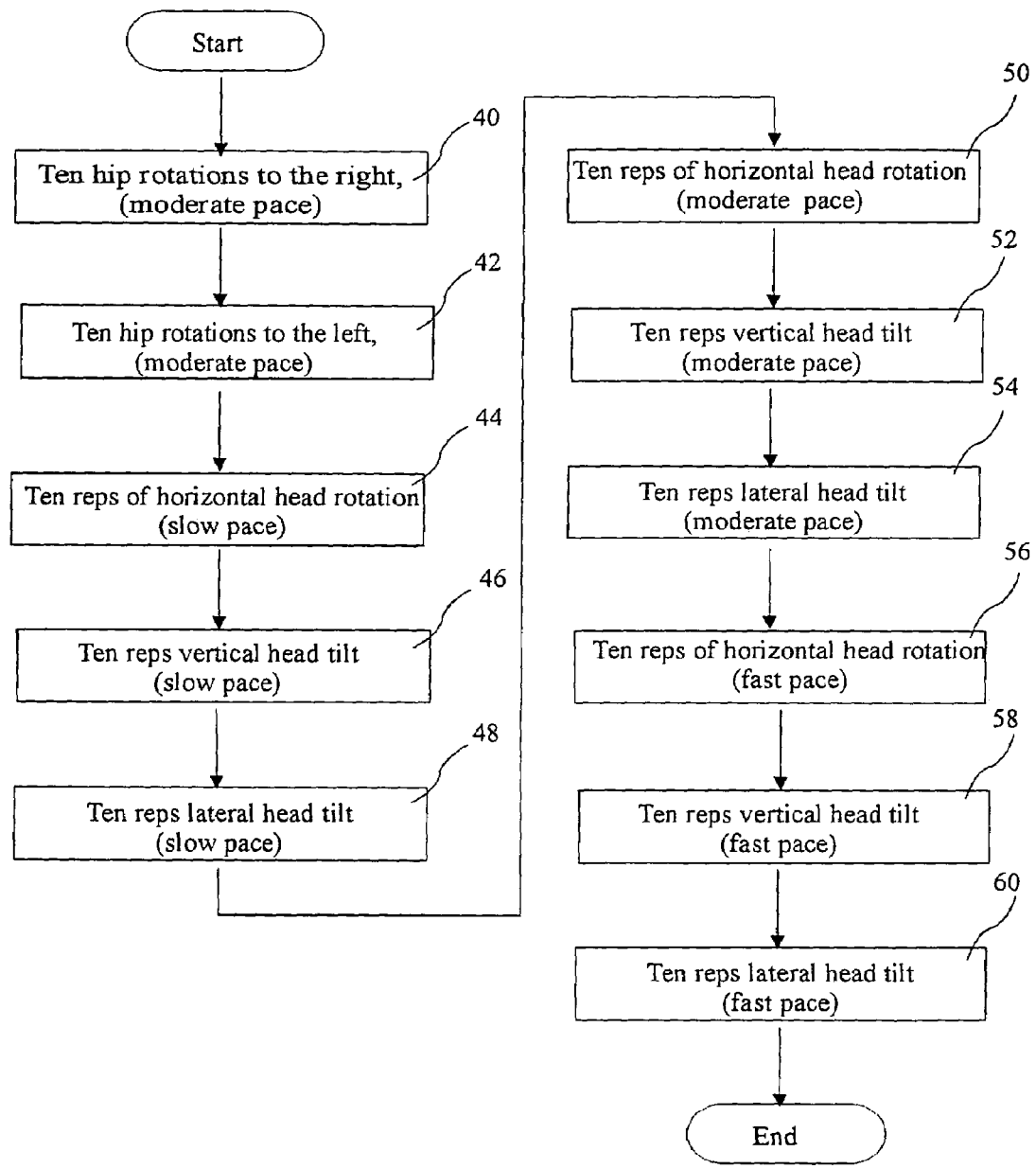
FIG. 3 shows a method for performing the warm-up exercises according to the present invention.

Ultimately, the exercises preferably should be done as shown in FIG. 3 as follows: about ten repetitions of the hip rotation exercise to right—moderate pace 40; about ten repetitions of the hip rotation exercise to left—moderate pace 42; one set of ten repetitions of the horizontal head rotation exercise—slow pace 44; one set of about ten repetitions of the vertical tilt exercise—slow pace 46; one set of about ten repetitions of the lateral tilt exercise—slow pace 48; one set of about ten repetitions of the horizontal head rotation exercise—moderate pace 50; one set of about ten repetitions of the vertical tilt exercise—moderate pace 52; one set of about ten repetitions of the lateral tilt exercise—moderate pace 54; one set of about ten repetitions of the horizontal head rotation exercise—fast pace 56; one set of about ten repetitions of the vertical tilt exercise—fast pace 58; one set of about ten repetitions lateral tilt exercise—fast pace 60. In each exercise, the user should preferably build up to a maximum of ten repetitions. The warm-up exercises prepare the user to go into the conditioning exercises.

Figure 4:
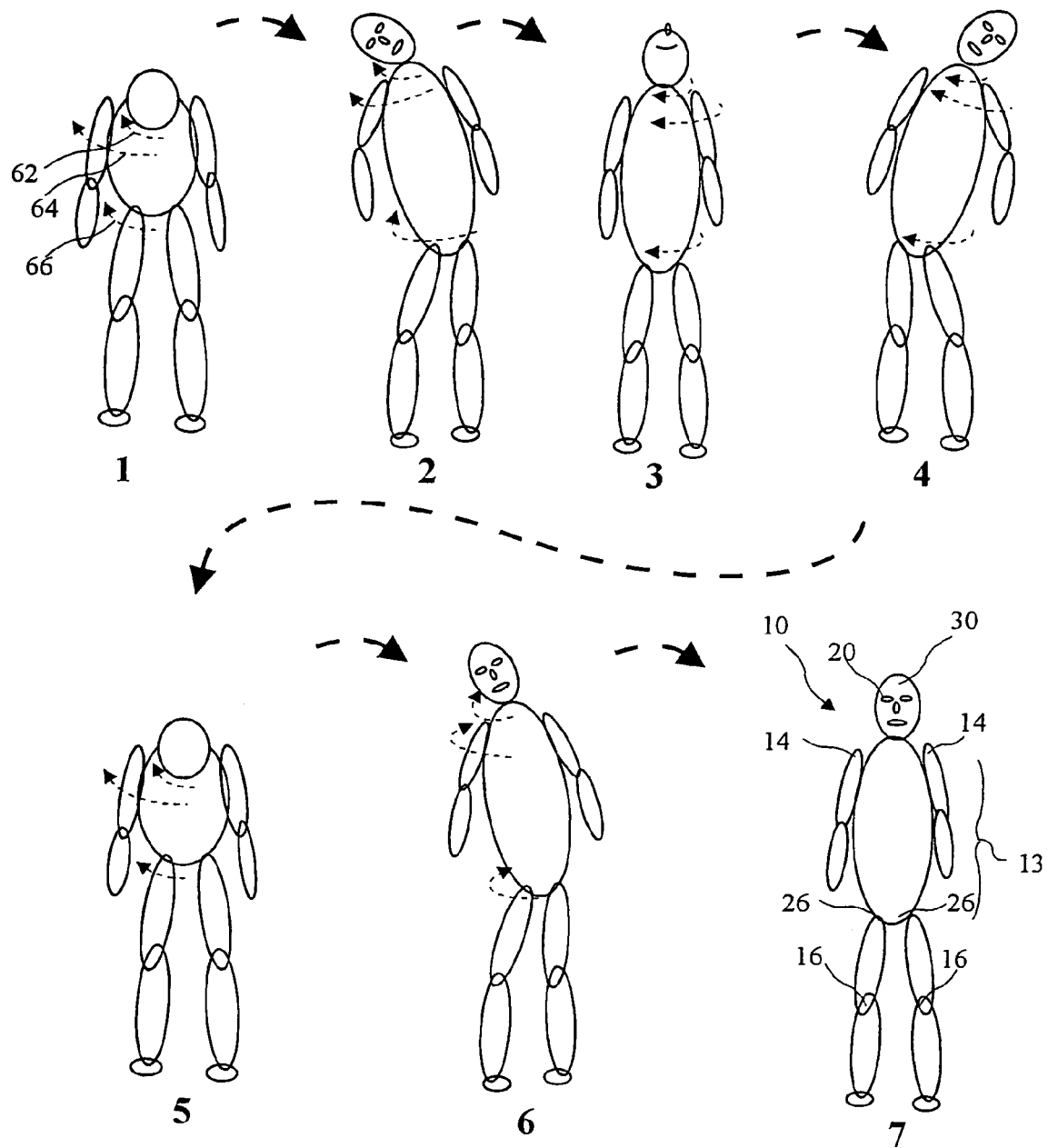
FIG. 4 depicts a spiral conditioning exercise according to the present invention.

The first conditioning exercise called the spiral exercise is depicted in seven steps in FIG. 4. This is a continuous exercise (i.e., not a four count,) and the user 10 will preferably reach the extreme positions of the head tilt that occurred in the warm-up exercises (see FIGS. 2A-2D). Knees 16 are kept bent, shoulders 14 relaxed, feet 18 fixed, and eyes 20 open. The user 10 is instructed to begin to rotate the user's head 30 as indicates by second circle 62, begin to rotate the upper body 12 as indicated by third circle 64, and begin to rotate the hips 14 as indicated by fourth circle 66, all in a smooth right (i.e., clockwise) motion. The rotational movements continue along the circles 62, 64, and 66 moving to the right side, backwards, left side, forwards, and continuing in circular movements through the motions depicted in FIG. 4. More specifically, as was done in the warm-up head tilt, the user 10 bends his or her head 30 down as shown in step 1, to the user's right as shown in step 2, back (i.e., rearward) as shown in step 3, to the left side as shown in step 4, and down again as shown in step 5 as the circle is made. After three or four rotations when a smooth and steady pace is achieved, the user should spiral (i.e., decrease the amplitude of the variation from standing vertically as shown in step 6) to a stop standing vertically as shown in step 7.

The user may experience a mild queasiness and/or dizziness after the spiral exercise, and the room may appear to be moving, which is perfectly normal and, in fact, this is the preferred response in order to begin gradual conditioning. The user 10 may steady themself on the support 24 (see FIG. 1B) in front of the user 10 for a few moments until the queasiness and/or dizziness subsides, if the use 10 desires. The queasiness and/or dizziness should go away within a minute or two, but if the feeling of queasiness and/or dizziness continues after a few minutes, the day's session should be ended, and the exercises continued (starting again with the warm-up exercises) the following day.

The user 10 should work up to doing the spiral exercise a total of six times (i.e., six sets of three or four rotations each), beginning with a clockwise spiral and then a counterclockwise spiral, alternating until three in each direction have been done. As the body becomes conditioned to the spiral exercise, and the user no longer experiences the mild queasy feeling, the pace of rotation should be increased in order to create the mild queasy feeling which is an indication that the exercise will bring about conditioning.

Figure 5:
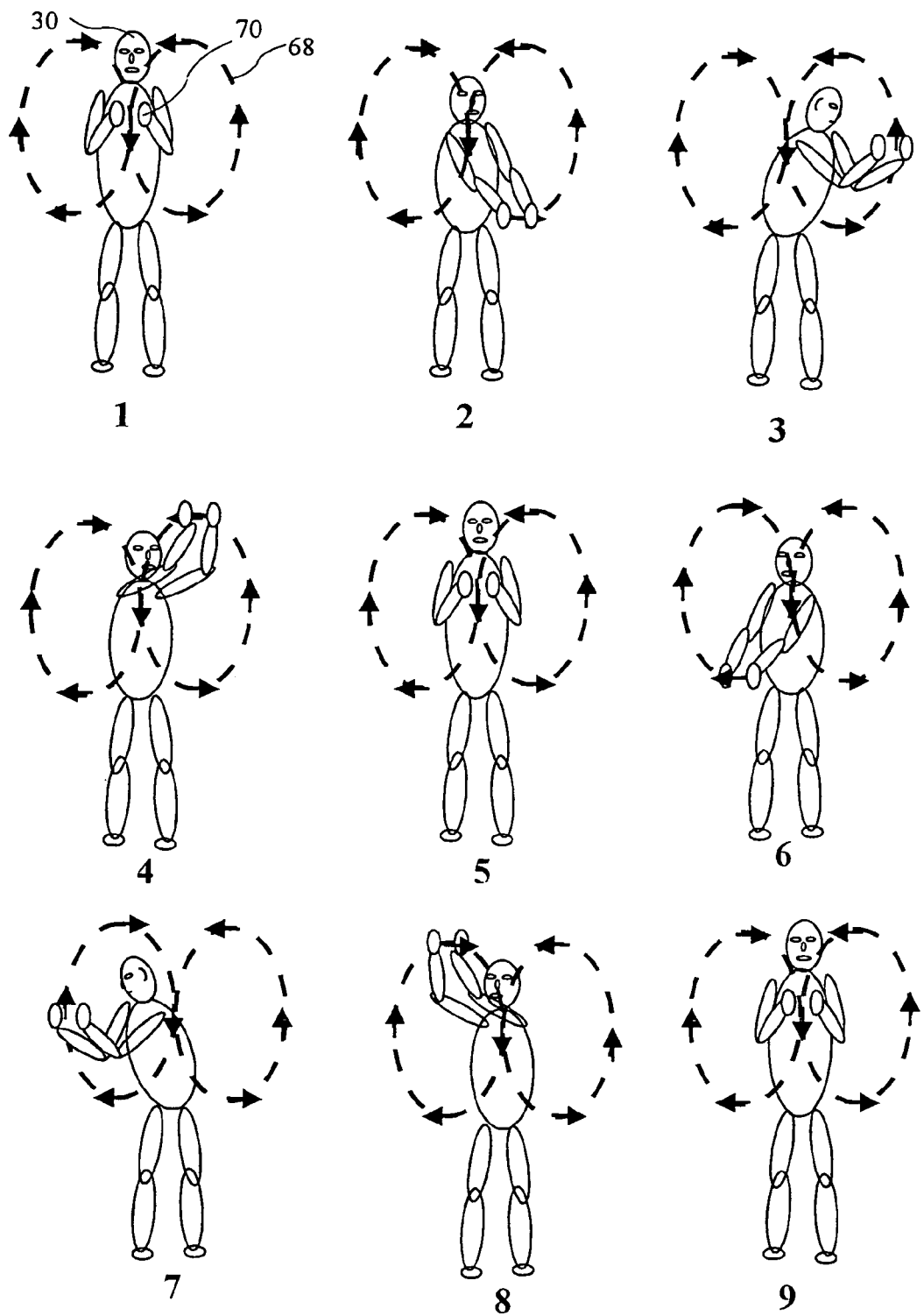
FIG. 5 depicts a figure eight exercise according to the present invention.

The next conditioning exercise is referred to as the figure eight exercise shown in FIG. 5. The figure eight exercise may be described as having the user visualize a very long paint brush in the user's mouth (or alternatively, projecting from the user's head 30) and painting a large lazy eight 68 figure (i.e., a figure eight laying on it's side) on a curved vertical wall in front and partially wrapping around each side of the user 10. The user 10 should begin slowly until the user 10 is comfortable and confident that the figure eight exercise is being done correctly. The upper body 13 and hips 26 (see FIGS. 1A, 1B) should be relaxed and may follow the movement of the head 30. The user's hands 70 should trace out the lazy eight 68 as if they are guiding the imaginary paint brush on the wall, with the user's head following the motion of the paint brush.

Continuing with FIG. 5, the user 10 should stand erect and looking forward (step 1) begin an upward sweep figure eight exercise by sweeping the hands 70 downward, and then to the left (step 2) following the motion of the hands 70 with the head 30. The user 10 then continues tracing the lazy eight 68 with an upward sweep of the head 30 and hands 70 on the left end of the lazy eight 68 (step 3). The user 10 continues sweeping the hands 70 and head 30 to a top left position in step 4, and back to the standing erect position (step 5). The user 10 then traces the right side of the lazy eight 68 (steps 6, 7, and 8,) returning to the standing erect position (step 9). To do one figure eight exercise, the user 10 must trace three or four of the lazy eights 68 then stop abruptly in the standing erect position.

Figure 6:
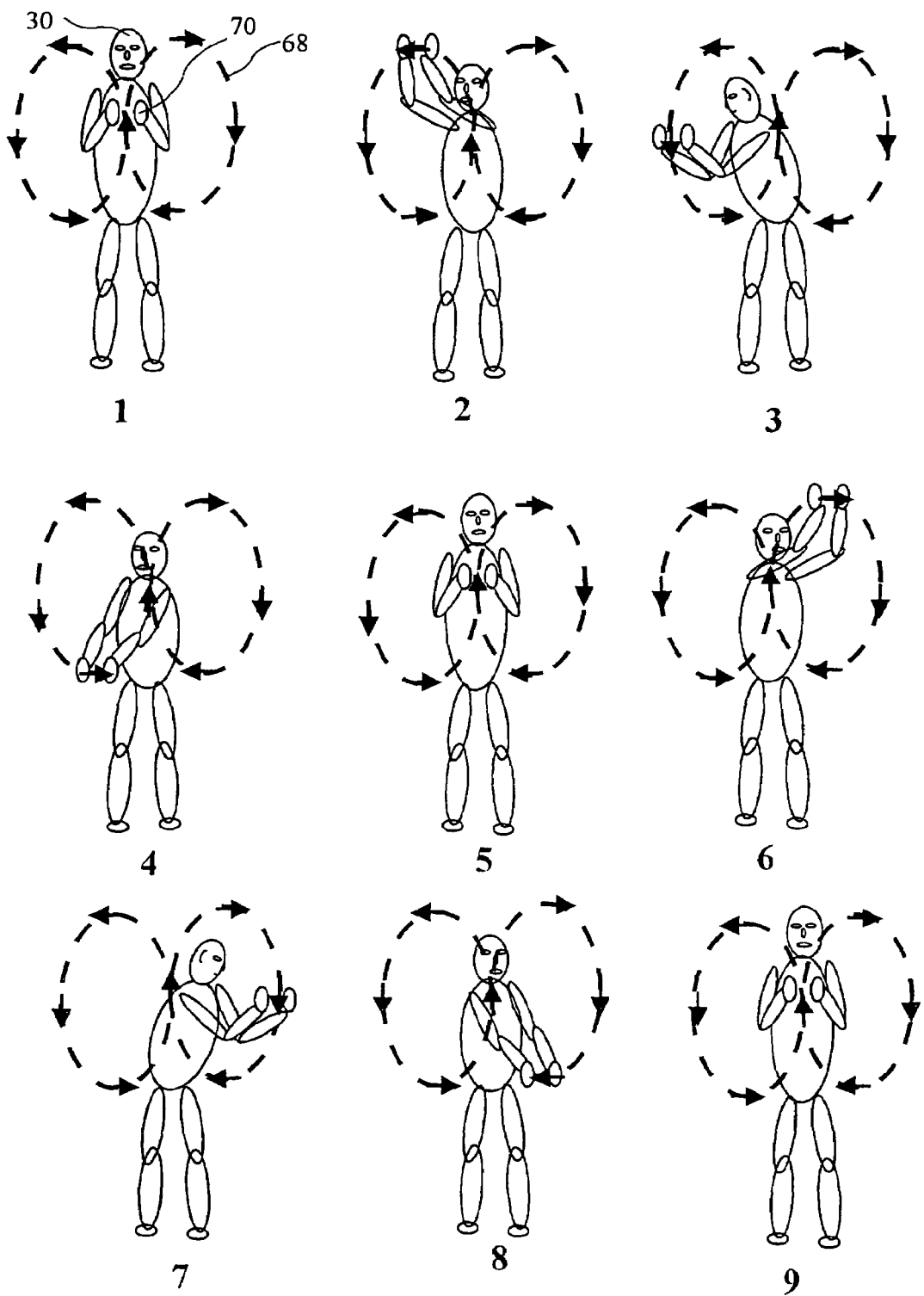
FIG. 6 depicts a second figure eight exercise according to the present invention.

The user 10 then begins a downward sweep figure eight exercise as shown in FIG. 6. The user 10 should stand erect and looking forward (step 1) begin a downward sweep figure eight exercise by sweeping the hands 70 upward, and then to the right (step 2) following the motion of the hands 70 with the head 30. The user 10 then continues tracing the lazy eight 68 with a downward sweep of the head 30 and hands 70 on the right end of the lazy eight 68 (step 3). The user 10 continues sweeping the hands 70 and head 30 to a bottom right position in step 4, and back to the standing erect position (step 5). The user 10 traces the left side of the lazy eight 68 (steps 6, 7, and 8), returning to the standing erect position (step 9). The user 10 then performs four more figure eight exercises, alternating between upward sweep figure eight exercises with the upward sweep of the head 30 and hands 70 at the ends of the lazy eight 68 as shown in FIG. 5, and downward sweep figure eight exercises with the downward sweep of the head 30 and hands 70 at the ends of the lazy eight 68 as shown in FIG. 6.

The figure eight exercise is a very effective exercise that will quickly test the limit of the user's motion tolerance level. Therefore, the figure eight exercise should be done at a comfortable pace for the user 10. The user 10 should work up to doing six figure eight exercises, beginning with an upward sweep figure eight exercise following by a downward sweep figure eight exercise, alternating the motion doing a total of three figure eight exercises in each direction. The user 10 should pause between each figure eight exercise to allow any symptoms to go away.

Figure 7:
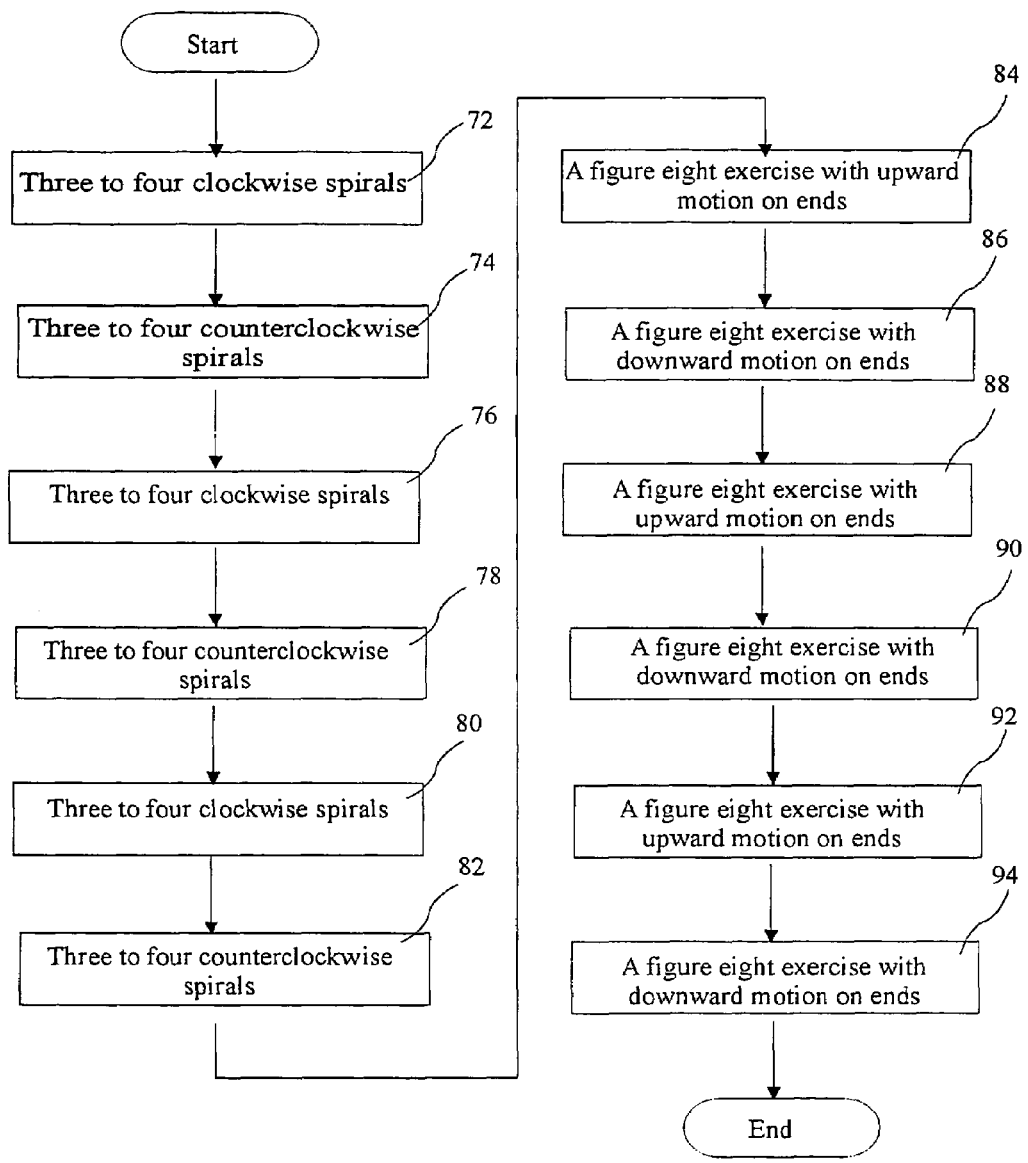
FIG. 7 shows a method for performing the conditioning exercises according to the present invention.

The conditioning exercises preferably are performed as shown in FIG. 7. The user 10 performs three to four clockwise spiral exercises (see FIG. 4) in step 72 and three to four counter clockwise spiral exercises in step 74. The clockwise, and then counter clockwise spirals are repeated in steps 76, 78, 80, and 82. The user 10 then performs a figure eight exercise with upward motion on the ends of the lazy eight 68 (see FIG. 5) at step 84 and then a figure eight exercise with downward motion on the ends of the lazy eight 68 (see FIG. 6) at step 86. The upward and then downward figure eight exercises are repeated in steps 88, 90, 92, and 94.

Preferably, a reference guide and daily exercise log is provided with the video to remind the user of the order in which the exercises are done and to help the user track his progress in the conditioning process.

Near the end of the two week conditioning period, it is beneficial to start a transference process wherein the user 10 engages in the activity that causes the motion sickness. However, the user 10 should limit his/her exposure time to this activity. For example, if reading while traveling causes the user motion sickness, he/she should read only until mild symptoms appear. Once the conditioning takes place, it never goes away completely. With continued periodic exposure to the motion sickness causing activity, there may be no future need to preform the conditioning exercises. However, the user's tolerance level to certain motions may slowly diminish over time if he/she does not periodically experience that motion. If this happens, the exercises should be done for a few days, and former motion tolerance levels will be regained quickly.

A preferred method of teaching the exercises described above is through self supervised viewing of a recorded media. The recorded media may be a motion picture film, VHS, 8 mm or any other video tape format, a DVD, a solid state memory, or any other recorded media. The recorded media may also be downloaded through the Internet, cable or satellite television services, or any downloadable media. The recorded media preferably includes a sound track, but may be subtitled or have text appended in some other manner. The recorded media preferably includes both an explanation of the exercises, and a recorded demonstration of the exercises described above in FIGS. 2A through 7 performed by a demonstrator.

While the invention herein disclosed has been described by means of specific embodiments and applications thereof, numerous modifications and variations could be made thereto by those skilled in the art without departing from the scope of the invention set forth in the claims.

We claim:

1. A method for teaching exercises to a user for conditioning to reduce symptoms of motion sickness, the method comprising:
    recording a demonstrator on a recording medium, the demonstrator performing a series of hip, upper body, hand, and head exercises, the series of exercises comprising individual exercises of:
        performing warm-up exercises;
        simultaneously rotating the hips, the upper body, and the head, wherein the demonstrator spirals to a stop to demonstrate a spiral exercise; and
        simultaneously weaving the hands and head through an imaginary lazy eight figure to demonstrate a figure eight exercise, and
    recording instructions on performing the exercises, wherein the conditioning exercises are self-directable by the user.

2. The method for teaching of claim 1, wherein recording the demonstrator comprises recording the demonstrator standing proximal to a support.

3. The method for teaching of claim 1, wherein recording the demonstrator comprises recording the demonstrator standing with back straight, shoulders relaxed, knees slightly bent, feet about shoulder width apart, and eyes open and looking forward and in line with the nose.

4. The method for teaching of claim 1, wherein the performing warm-up exercises step comprises:
    rotating the hips to demonstrate a hip rotation exercise;
    horizontally rotating the head to demonstrate a horizontal head rotation exercise;
    vertically tilting the head to demonstrate a vertical head tilt exercise; and
    laterally tilting the head to demonstrate a lateral head tilt exercise.

5. The method for teaching of claim 4, wherein demonstrating the horizontal head rotation exercise comprises rotating the head using a count of four, wherein the demonstrator rotates the head to the right, back to the center, to the left, and back to center, and wherein the demonstrator pauses briefly at each count point.

6. The method for teaching of claim 4, wherein demonstrating the vertical head tilt exercise comprises tilting the head forward and backward using a count of four, wherein the demonstrator tilts the head forward, up, back, and up, and wherein the demonstrator pauses briefly at each count point.

7. The method for teaching of claim 4, wherein demonstrating the lateral head tilt exercise comprises tilting the head side to side using a count of four, wherein the demonstrator tilts the head right, center, left, and back to center, and wherein the demonstrator pauses briefly at each count point.

8. The method for teaching of claim 4, wherein the recording instructions step includes recording instructions to first perform the hip rotation exercise about ten times to the right and then to perform the hip rotation exercise about ten times to the left, and then to perform the horizontal head rotation exercise, the vertical head tilt exercise, and lateral head tilt exercise.

9. The method for teaching of claim 4, wherein the recording instructions step includes recording instructions to first perform the hip rotation exercise and then to perform three sets of the horizontal head rotation exercise, the vertical head tilt exercise, and lateral head tilt exercise.

10. The method for teaching of claim 9, wherein the recording instructions step includes recording instructions to perform:
    a first set of about ten repetitions of the horizontal head rotation exercise, about ten repetitions of the vertical head tilt exercise, and about ten repetitions of lateral head tilt exercise;
    a second set of about ten repetitions of the horizontal head rotation exercise, about ten repetitions of the vertical head tilt exercise, and about ten repetitions of lateral head tilt exercise; and a third set of about ten repetitions of the horizontal head rotation exercise, about ten repetitions of the vertical head tilt exercise, and about ten repetitions of lateral head tilt exercise.

11. The method for teaching of claim 10, wherein the recording instructions step includes recording instructions to perform the first set at a slow pace, the second set at a moderate pace, and the third set at a fast pace.

12. The method for teaching of claim 4, wherein the recording instructions step includes recording instructions to initially perform the warm-up exercises at a slow pace and to increase the pace on subsequent days.

13. The method for teaching of claim 4, wherein:
the horizontally rotating the head to demonstrate the horizontal head rotation exercise comprises the horizontally rotating the head while holding the shoulders substantially fixed; and
the vertically tilting the head to demonstrate a vertical head tilt exercise comprises the vertically tilting the head while holding the shoulders substantially fixed.

14. The method for teaching of claim 1, wherein demonstrating the spiral exercise comprises:
rotating smoothly with the feet fixed;
bending the head and upper body down, to the side, back, to the other side, and down again in each rotation;
reaching the amount of the head tilt that occurred in the warm-up exercises; and
after at least three rotations, spiraling to an erect standing position.

15. The method for teaching of claim 14, wherein demonstrating the spiral exercise comprises demonstrating the spiral exercise with knees kept bent, shoulders relaxed and eyes open.

16. The method for teaching of claim 14, wherein the recording instructions step includes recording instructions to perform a total of six of the spiral exercises, alternating between clockwise rotation and counterclockwise rotation.

17. The method for teaching of claim 14, wherein the recording instructions step includes recording instructions to increase the rate of rotation of the spiral if a queasy feeling does not result from the spiral exercise.

18. The method for teaching of claim 14, wherein the recording instructions step includes recording instructions to discontinue the conditioning exercises until the next day if the spiral exercise results in a queasy feeling which lasts for more than about two minutes.

19. The method for teaching of claim 1, wherein demonstrating the figure eight exercise comprises:
visualizing a very long paint brush projecting from the demonstrator's head and painting large lazy eight figures on an imaginary curved vertical wall in front and partially wrapping around each side of the demonstrator;
relaxing upper body and hips and following the painting motion of the head with the upper body and hips;
tracing out the lazy eight figures with the hands as if guiding the paint brush; and
stopping abruptly in the original standing position.

20. The method for teaching of claim 19, wherein demonstrating the figure eight exercise further comprises:
performing an upward figure eight exercise with upward sweeps on ends of the lazy eight figures and tracing out at least six lazy eight figures;
performing a downward figure eight exercise with downward sweeps on the ends of the lazy eight figures and tracing out at least six lazy eight figures; and
repeating the two previous steps at least two more times.

21. A conditioning exercise involving motion of the central body, head, upper body, hips, and arms, the exercise comprising the steps of:
performing warm-up exercises with back straight, shoulders relaxed, knees slightly bent, feet about shoulder width apart, and eyes kept open and looking forward, the warm-up exercises comprising:
rotating the hips;
rotating the head using a count of four, wherein the head is rotated to the right to a first count point, back to the center to a second count point, to the left to a third count point, and back to center to a fourth count point, with brief pauses at each count point;
tilting the head forward and backward using a count of four, wherein the head is tilted forward, up, back, and up, with brief pauses at each count point; and
tilting the head side to side using a count of four, wherein the head is tilted to right, center, left, and back to center, with brief pauses at each count point,
performing conditioning exercises comprising:
spiraling the upper body, the head, and the hips comprising:
rotating smoothly with the feet fixed;
bending the head down, to the side, back, to the other side, and down again in each rotation;
reaching the amount of the head tilt that occurred in the warm-up exercises; and
after at least three rotations, spiraling to a standing position; and
weaving the arms in a figure eight comprising:
visualizing a very long imaginary paint brush projecting from the head and painting large lazy eight figures on a curved vertical wall in front and partially wrapping around each side of the demonstrator;
relaxing upper body and hips and following the painting motion of the head with the upper body and hips;
tracing out the lazy eight figures with the hands as if guiding the imaginary paint brush; and
stopping abruptly in the standing position.

22. An exercise program involving motion of the central body, head, upper body, hips, and arms, the exercise comprising the steps of:
performing warm-up exercises with back straight, shoulders relaxed, knees slightly bent, feet about shoulder width apart, and eyes kept open and looking forward, the warm-up exercises comprising:
performing a hip rotation exercise about ten times to the right;
performing the hip rotation exercise about ten times to the left;
performing a first set of about ten repetitions of a horizontal head rotation exercise, about ten repetitions of a vertical head tilt exercise, and about ten repetitions of a lateral head tilt exercise, all at a slow pace;
performing a second set of about ten repetitions of the horizontal head rotation exercise, about ten repetitions of the vertical head tilt exercise, and about ten repetitions of lateral head tilt exercise; and
performing a third set of about ten repetitions of the horizontal head rotation exercise, about ten repetitions of the vertical head tilt exercise, and about ten repetitions of lateral head tilt exercise;
performing conditioning exercises comprising:
simultaneously clockwise rotating the hips, the upper body, and the head, and spiraling to a stop after at least three rotations;

simultaneously counterclockwise rotating the hips, the upper body, and the head, and spiraling to a stop after at least three rotations;

repeating the clockwise and counterclockwise rotations at least two more times each;

performing a first figure eight exercise with upward sweeps on ends of a lazy eight figure and tracing out at least six lazy eight figures;

performing a second figure eight exercise with a downward sweep on the ends of the lazy eight figure and tracing out at least six lazy eight figures; and repeating the first and second figure eight exercises at least two more times.

* * * * *